United States Patent
Patel et al.

(10) Patent No.: US 6,849,456 B2
(45) Date of Patent: Feb. 1, 2005

(54) TEST STRIP QUALIFICATION SYSTEM

(75) Inventors: Harshad Patel, Fremont, CA (US); James Witt, Sunnyvale, CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 10/712,680

(22) Filed: Nov. 12, 2003

(65) Prior Publication Data

US 2004/0106212 A1 Jun. 3, 2004

Related U.S. Application Data

(63) Continuation of application No. 10/100,254, filed on Mar. 14, 2002, now Pat. No. 6,682,933.

(51) Int. Cl.$^7$ .......................... G01N 31/00; G01N 33/86
(52) U.S. Cl. ............................... 436/8; 436/69; 435/13; 600/369; 73/64.41; 702/19; 702/32
(58) Field of Search ................................ 436/8, 63, 69, 436/180; 422/73, 100; 435/13; 600/368, 369; 73/64.41; 702/19, 31, 32

(56) References Cited

U.S. PATENT DOCUMENTS

| | | |
|---|---|---|
| 5,230,866 A | 7/1993 | Shartle et al. |
| 5,504,011 A | 4/1996 | Gavin et al. |
| 5,591,403 A | 1/1997 | Gavin et al. |
| 6,084,660 A | 7/2000 | Shartle |
| 6,261,519 B1 | 7/2001 | Harding et al. |
| 6,521,182 B1 | 2/2003 | Shartle et al. |
| 6,682,933 B2 * | 1/2004 | Patel et al. ..................... 436/8 |
| 2001/0004641 A1 | 6/2001 | Hawkins |
| 2002/0064480 A1 | 5/2002 | Shartle |
| 2002/0098114 A1 | 7/2002 | Harding et al. |
| 2002/0110486 A1 | 8/2002 | Shartle et al. |
| 2002/0110922 A1 | 8/2002 | Shartle et al. |
| 2003/0031594 A1 | 2/2003 | Shartle et al. |
| 2003/0044318 A1 | 3/2003 | Olson |
| 2004/0043440 A1 * | 3/2004 | Kermani ..................... 435/13 |

FOREIGN PATENT DOCUMENTS

| | | |
|---|---|---|
| EP | 0 974 840 A2 | 1/2000 |
| EP | 1.069.427 | 6/2001 |
| EP | 1.107.004 | 6/2001 |
| WO | WO 95/12127 | 5/1995 |
| WO | WO 01/75433 | 10/2001 |

* cited by examiner

*Primary Examiner*—Maureen M. Wallenhorst
(74) *Attorney, Agent, or Firm*—Carol M. LaSalle; Bozicevic, Field & Francis LLP

(57) ABSTRACT

In connection with a fluidic medical diagnostic device that permits measurement of the coagulation time of blood, software, methods and associated devices for quality control are provided. The fluidic device preferably includes a test strip with one end having a sample port for introducing a sample and a bladder at the other end for drawing the sample to a measurement area. A channel carries sample from the sample port to an assay measurement area and first and second control measurement areas. Preferably a stop junction, between the measurement areas and bladder, halts the sample flow for measurement. If results from measurements taken for each control fall within a predetermined zone or defined limits, the assay measurement is qualified. If not, an error is registered and the test strip is counted as unfit.

8 Claims, 3 Drawing Sheets

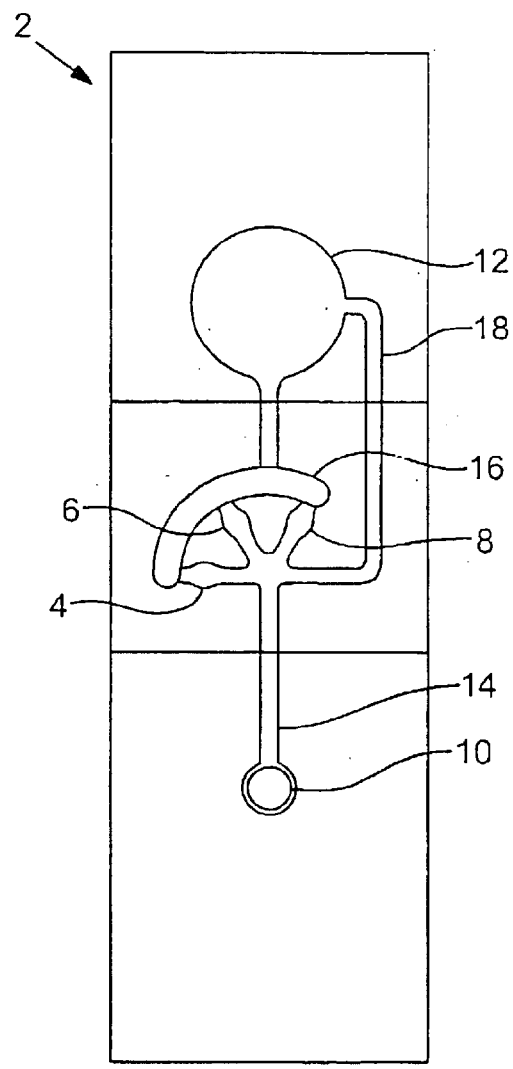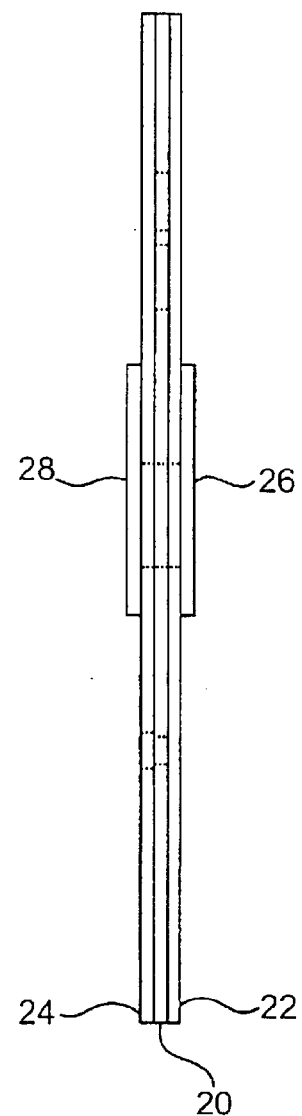
FIG. 1A
PRIOR ART
FIG. 1B
PRIOR ART

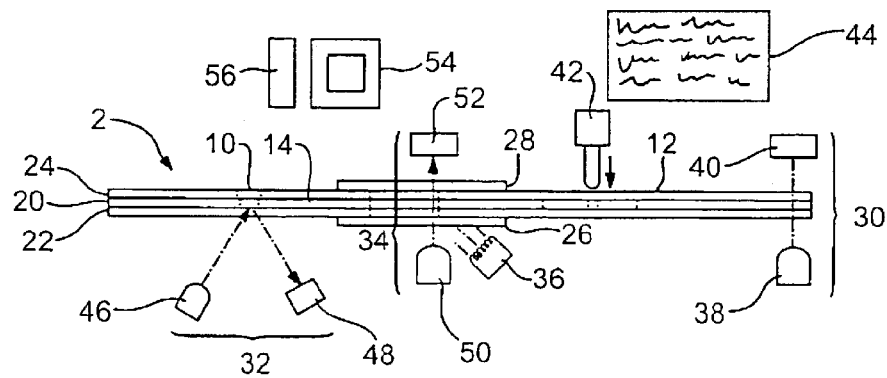
PRIOR ART FIG. 2A
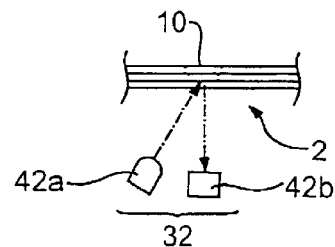
PRIOR ART FIG. 2B
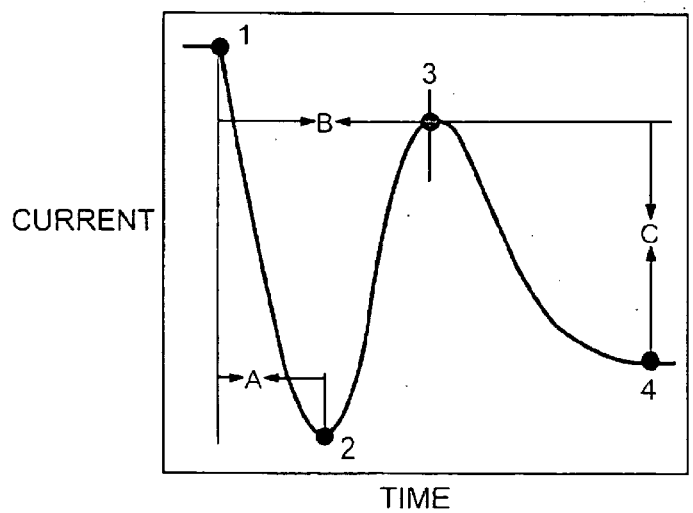
FIG. 3
PRIOR ART

TEST STRIP QUALIFICATION SYSTEM

This is a continuation of U.S. patent application Ser. No. 10/100,254, filed Mar. 14, 2002, now U.S. Pat. No. 6,682,933, issued on Jan. 27, 2004.

FIELD OF THE INVENTION

This invention relates to approaches for qualifying results obtained in using analyte test strips. The invention is particularly suited for testing the quality of test strips used for measuring prothrombin time (PT time) with whole blood in which a measurement area includes a composition that catalyzes the blood clotting cascade.

BRIEF DESCRIPTION OF THE DRAWINGS

FIGS. 1-3 represent information known in the art and are referenced in the Background of the Invention.

FIG. 1A is a top view of a test strip as may be used in connection with the present invention; FIG. 1B is a side view of the test strip.

FIG. 2A is a schematic of hardware elements for a meter for that may be used in the present invention; FIG. 2B shows an alternative variation of an element of the meter of FIG. 2A.

FIG. 3 is a graph of data that used to determine PT time.

FIG. 4 is a graph showing a qualification zone for an assay second control.

BACKGROUND OF THE INVENTION

Figure 4:
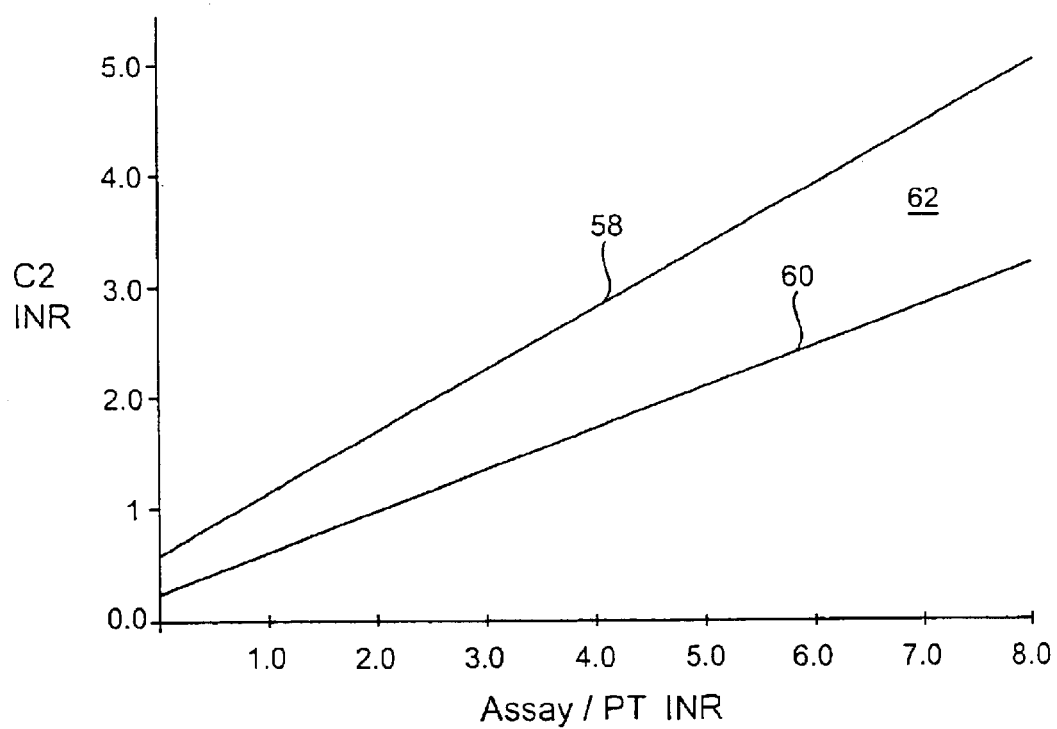
FIG. 4 diagrammatically illustrates aspects of the present invention. Variation of the invention from that shown in the figures is contemplated.

European patent application EP 0 974 840 the (840 publication), published Jan. 26, 2001, describes a device and system that may be used with the present invention. FIG. 1 presented herein as adapted from the 840 publication shows a parallel multi-channel test strip 2. In it, measurement areas 4, 6 and 8 are provided. Upon introducing a sample, usually whole blood, at introduction port 10 and depressing a bladder 12 and releasing it, a partial vacuum draws the blood though channel 14 up to shared stop junction 16. The test strip also includes a bypass channel 18 which draws sample toward bladder 12 to alleviate negative pressure at the stop junction order to prevent overcoming the surface tension that pins the fluid in the measurement areas at the stop junction.

For PT measurements, it is important to stop the flow of sample as it reaches that point to permit reproducible "rouleaux formation"—the stacking of red blood cells—which is an important step in monitoring blood clotting using the present invention. The principle of stop junction operation is described in U.S. Pat. No. 5,230,866.

A test strip body is described as preferably produced from three layers. The elements above are formed by cutouts in intermediate layer 20, sandwiched between a top layer 22 and bottom layer 24. Preferably, layer 22 is double-sided adhesive tape. Stop junction 16 is preferably formed by an additional cutout in layer 22 and/or 24, aligned with the cutout in layer 20 and sealed with sealing layer 26 and/or 28.

Each cutout for stop junction 16 is preferably at least as wide as channel 14. A filter may optionally be used to cover sample port 10. The filter separates red blood cells from a whole blood sample and/or may contain a reagent to interact with the blood to provide additional information. A suitable filter comprises an anisotropic membrane, preferably a polysulfone membrane of the type available from Spectral Diagnostics, Inc., (Toronto, Canada). An optional reflector may be on, or adjacent to, a surface or layer of test strip 2 and positioned over the measurement areas. If a reflector is present, the device becomes a transflectance device.

Typically, in producing the test strip, reagent is bubble-jet printed onto areas 4, 6 and 8. The chemicals at each site are disclosed in the 840 publication as: 1) thromboplastin in area 4; 2) thromboplastin bovine eluate, and recombinant Factor VIIa in area 6 and 3) thromboplastin and bovine eluate alone in area 8. The composition in area 6 is selected to normalize the clotting time-of a blood sample by counteracting the effect of an anticoagulant, such as warfarin. The composition in area 8 is selected to partially overcome the effect of an anticoagulent. The bovine eluate (plasma barium citrate bovine eluate) is available from Haemotologic Technologies, (Burlington, Vt.); recombinant Factor VIIa from American Diagnostica, (Greenwich, Conn.). Thromboplastin, from Ortho Clinical Diagnostics, (Raritan, N.J.).

After printing, a sample port is cut in untreated polyester film such as AR1235, available from Adhesives Research, (Glen Rock, Pa.) and then laminated, in register, to the top of the double-sided tape after removing the release layer. A die then cuts the stop junction through the three layers of the sandwich. Finally, strips of single-sided adhesive tape such as MSX4841, available from 3M, (St. Paul, Minn.) are applied to the outside of the polyester layers to seal the stop junction.

Use of the test strip can be understood with reference to a schematic of the elements of a meter shown in FIGS. 2A and 2B (also adapted from the 840 publication), which contemplates an automated meter. Alternatively, manual operation is also possible. In that case, bladder 12 is manually depressed before sample is applied to port 10, then released. The first step the user performs is to turn on the meter, thereby energizing strip detector 30, sample detector 32, measurement system 34, and optional heater 36. The second step is to insert the strip. Preferably, the strip is not transparent over at least a part of its area, so that an inserted strip will block the illumination by LED 38 of detector 40. (More preferably, the intermediate layer is formed of a non-transparent material, so that background light does not enter measurement system 34.) Detector 40 thereby senses that a strip has been inserted and triggers bladder actuator 42 to compress bladder 12. A meter display 44 then directs the user to apply a sample to sample port 10 as the third and last step the user must perform to initiate the measurement sequence. The empty sample port is reflective. When a sample is introduced into the sample port, it absorbs light from LED 46 and thereby reduces the light that is reflected to detector 48. That reduction in light, in turn, signals actuator 42 to release bladder 12. The resultant suction in channel 14 draws sample through the measurement areas to the stop junction. For each measurement area 4, 6 and 8, a LED 50 and detector 52 pair is provided to monitor the light transmitted through the sample as it is clotting.

Analysis of the transmitted light as a function of time (as described below) permits a calculation of the PT time, which is displayed on the meter display 44 and any messages regarding test strip fitness or reliability. Preferably, sample temperature is maintained at about 37° C. by heater 36. Each such function is controlled by a microprocessor chip 54 controlled by software stored in programmable, read-only memory 56.

As described above, the detector senses a sample in sample port 10, simply by detecting a reduction in (specular)

reflection of a light signal that is emitted by 46 and detected by 48. However, that simple system cannot easily distinguish between a whole blood sample and some other liquid (e.g,. blood serum) placed in the sample port in error or, even, an object (e.g., a finger) that can approach sample port 10 and cause the system to erroneously conclude that a proper sample has been applied.

To avoid this type of error, another embodiment measures diffuse reflection from the sample port. This embodiment appears in FIG. 2B, which shows detector 48 positioned normal to the plane of strip 2. With the arrangement shown here, if a whole blood sample has been applied to sample port 10, the signal detected by 48 increases abruptly, because of scattering in the blood sample, then decreases, because of rouleaux formation. The detector system 32 is thus programmed to require that type of signal before causing actuator 42 to release bladder 12. The delay of several seconds in releasing the bladder does not substantially affect the readings described below.

FIG. 3 depicts a typical "clot signature" curve in which current from detector 50 is plotted as a function of time. Blood is first detected in a measurement area at time 1. In the time interval A, between points 1 and 2, the blood fills the measurement area. The reduction in current during that time interval is due to light scattered by red cells and is thus an approximate measure of the hematocrit. At point 2, sample has filled the measurement area and is at rest, its movement having been stopped by the stop junction. The red cells begin to stack up like coins (rouleaux formation). The rouleaux effect allows increasing light transmission through the sample (and less scattering) in the time interval between points 2 and 3. At point 3, clot formation ends rouleaux formation and transmission through the sample reaches a maximum. The PT time can be calculated from the interval B between points 1 and 3 or between 2 and 3. The result is typically reported in terms of its "INR" (i.e.,International-Normalized Ratio). Thereafter, the blood changes state from liquid to a semi-solid gel, with a corresponding reduction in light transmission. The reduction in current (C) between the maximum 3 and endpoint 4 correlates with fibrinogen in the sample.

Measurements made on a whole blood sample using the strip yield a curve of the type shown in FIG. 3 for each of the measurement areas. The data from the curves for the controls (measurement areas 6 and 8) are used to qualify the data from the curve for measurement area 4. The measurement of sample from area 4 is validated only when measurements on areas 6 and 8 yield results within a predetermined range. If either or both of these control measurements are outside the range, then a retest with another test strip is indicated. Ageing or oxidization of reagents can potentially yield failing Control 1 an/or Control 2 tests.

SUMMARY OF THE INVENTION

In connection with such a two-control test strip such as described in the '840 publication, the present invention applies certain criteria to produce a highly-accurate test strip qualification process based on results obtained from each control. Results from the first control (C1) are qualified if they fall within a simple numerical range. Where results are expressed in terms of INR, C1 readings at or between about 0.60 and 1.9 INR are acceptable. Results from the second control (C2) are qualified if they fall within a zone or region bounded by functions dependent upon assay PT time. When results from the second control and assay are expressed in terms of INR, the functions are line functions, diverging from one another at higher assay INR values. As in the referenced system, test strip results are qualified, or determined to be fit or reliable, upon both C1 and C2 results falling within the prescribed ranges.

Systems of the present invention preferably operate in connection with a disposable test strip and hand held meter as described above. Mathematical algorithms or functions, preferably those described in detail below, are used to qualify test strip data in a highly accurate manner as evidenced by exemplary results. Such results are preferably accomplished with a hand-held meter in a rapid fashion. The algorithms as implemented by hardware as well as the methodology disclosed form aspects of the present invention.

DETAILED DESCRIPTION OF THE INVENTION

In describing the invention in greater detail than provided in the Summary above, the subject test strip qualification system and methods for its use are described in relation to FIG. 4 and various equations. Before the present invention is described in such detail, however, it is to be understood that this invention is not limited to particular variations set forth and may, of courses vary. Various changes may be made to the invention described and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims made herein.

Furthermore, where a range of values is provided, it is understood that every intervening value, between the upper and lower limit of that range and any other stated or intervening value in that stated range is encompassed within the invention. The upper and lower limits of these smaller ranges may independently be included in the smaller ranges and is also encompassed within the invention, subject to any specifically excluded limit in the stated range. Where the stated range includes one or both of the limits, ranges excluding either both of those included limits are also included in the invention. Also, it is contemplated that any optional feature of the inventive variations described herein may be set forth and claimed independently, or in combination with any one or more of the features described herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are described. All existing subject matter mentioned herein (e.g., publications, patents, patent applications arid hardware) is incorporated by reference herein in its entirety. The referenced items are provided solely for their disclosure prior to the filing date of the present application. Nothing herein is to be construed as an admission that the present invention is not entitled to antedate such material by virtue of prior invention.

Also, it is noted that as used herein and in the appended claims, the singular forms "a," "and," "said" and "the" include plural referents unless the context clearly dictates otherwise. Conversely, it is contemplated that the claims may be so-drafted to require singular elements or exclude any optional element indicated to be so here in the text or drawings. This statement is intended to serve as antecedent basis for use of such exclusive terminology as "solely," "only" and the like in connection with the recitation of claim elements or the use of a "negative" claim limitation(s).

The present invention is preferably practiced with the test strip and procedured disclosed in connection with the '840 publication. According to the present invention, C1 includes sufficient coagulation factors to counteract any effect of anticoagulant—Coumadin in particular—in the blood sample to preferably produce a PT for C1 between 0.8 and 1.9 in a good-quality test strip. C2 differs form C1 both in the composition (as indicated above) and quantity of coagulation factors present in the reagent formulation. Fewer factors are added to C2 to create a partial normalization of the effects of the anticoagulant in the blood sample. Reaction area 6—corresponding to C1—preferably includes recombinant tissue factor with buffers and preservatives, bovine coagulation factors of the extrinsic pathway, and recombinant factor VIIa protein. Reaction area 8—corresponding to C2—preferably includes recombinant tissue factor with buffers and preservatives, bovine coagulation factors of the extrinsic pathway.

In qualifying test strips, measurements are preferably made on whole blood sample at each of the three test strip measurement areas, yielding curves of the type shown in FIG. 3 used to determine an INR value for each well. First, whole blood sample is drawn into each of the reaction areas so that the fluid rehydrates the dried reagents and reacts at each site. The data obtained for control wells 6 and 8 are used to qualify the data from the curve from measurement area 4 providing PT time. The test results, including that for the controls, is preferably converted to INR results for use in the algorithms described below and reporting results to the user.

Based on multiple test strip lots evaluated at multiple clinical sites, it was determined that sufficiently accurate qualification of test strips results if the PT INR for C1 has an upper limit of about 1.9 and a lower limit of about 0.60 (instead of the more modest range indicated above). As for C2 qualification results, is has been observed that C2 follows a linear or proportional relationship with the assay results obtained. Again, data from multiple test strip lots and clinical sites was used to generate qualification criteria.

The qualification criteria for C2 may be represented as lines with slightly different slopes and y-intercept values. The slope an upper limit line 58 as seen in FIG. 4 is greater than that of a lower limit line 60 also seen therein. The lines diverge from one another at higher PT values, thus creating a C2 widening qualification zone 62.

For the second control upper limit 58, when expressed in the form y=mx+b, with m≈0.56 to 0.58 and b≈0.90 the line produce provides an excellent fit to test data generated. For the second control lower limit 60, when expressed in the form y=mx+b, with m≈0.36 and b≈0.37 to 0.38 the line produce provides an excellent fit to test data generated. By use of the "≈" sign, it is meant equals or is about equal.

In actuality, the line equations described above may been defined with greater precision. Two significant figures are expressed in order to indicate that variation on such an order is contemplated. (The same holds true for C1 qualification criteria.) Still, FIG. 4 is drawn with the precision to which the invention is preferably practiced.

This being said, substantial variability in approach is contemplated as part of the present invention. For instance, one or more polynomial equations may be used to set the bounds, especially for C2. Alternately, tabular data representing results within each qualification ranges for C1 and C2, respectively, may be employed. In any event, various qualification zones or regions are defined. Further variation may include modifying C1 and C2 chemicals. While altering the chemistry may affect the characteristics of the functions defining the qualification zones, the general nature of the present invention should not change.

In instances where C1 and C2 results are qualified, the test strip meter display 44 shows PT time for the assay (preferably in terms of an INR value). If either or both of these control measurements are outside the ranges defined, another sort of message indicating test reliability or fitness is displayed by the test strip meter. Error messages specific to they type of failure may be presented (i.e., messages indicative of C1, C2 or C1 and C2 failure). Alternately, a retest with another test strip may simply be indicated.

EXAMPLES

A series of trials were conducted in connection, with the present invention as early as March 2000. These trials were of an experimental nature, necessary to determine and/or verify the accuracy of the test strip qualification approach taught herein. The results of such testing gave positive indication of sufficient accuracy in test strip accuracy achieved through use of the present invention. As of the filing date for this Specification, no product according to the present invention has yet been made available to the public.

The accuracy of the inventive methods function was first studied in connection with subjects enrolled at three independent institutions for evaluation against test strips as described above. In such clinical trials, venous blood was drawn and tested on a reference clinical laboratory device. These results were used for absolute reference. By comparison through expanded agreement analysis, which considers comparison of the clinical interpretation of test results versus the ultimate laboratory reference system, inventive system produced a 99% clinical agreement. This rate of agreement evinces significant improvement over the approach of the CoaguCheck meter by Roche Diagnostics (formerly Boehringer Mannheim Corp.) that produced a published performance of 87% expanded agreement vs. laboratory reference. A test strip error frequency of about 0.5% was observed in connection with these clinical trials for the present invention.

Lay person trials were also conducted on patients who tested themselves at four defined time intervals in the home environment with the subject test strip and meter and were than listed within four hours using venous blood for the reference laboratory system. The home environment/end user results were compared with the clinical results. This trial also produced an error frequency consistent with the first study at about 0.5%. A 0.5% error frequency rate was observed in connection with C1 and 0.5% with C2. Errors registered for both C1 and C2 occurred at a 0.1% frequency rate.

In running multiple other tests for verifying test strip accuracy, clinical accuracy of layperson end-users versus the laboratory reference device was determined to be in 95% clinical agreement using expanded agreement of result analysis.

Using the cumulative frequency approach, the accuracy of the subject invention as preferably practiced in the hands of the layperson end-user in comparison to the laboratory reference can be stated such that 94% of the time, the end-use obtains results within 0.5 INR units of the laboratory reference method. This shows a significant improvement over a corresponding 90% performance rating for results within 0.5 INR as published in connection with Avocet Medical products.

Though the invention has been described in reference to a single example, optionally incorporating various features, the invention is not to be limited to what is described or indicated as contemplated with respect to possible variation. The breadth of the present invention is to be limited only by the literal or equitable scope of the following claims. That being said,

We claim:

1. A system for testing the qualification of a test strip for use to measure prothrombin (PT) time, said test strip comprising an assay reaction area and a control reaction area, said system comprising:
   a meter configured for receiving said test strip; and
   a computer-readable medium embodying a program to qualify said test strip according to a method comprising:
      obtaining PT results for said control reaction area; and
      comparing results from said control reaction area to control qualification criteria comprising an upper limit and a lower limit, said upper limit being about a 1.9 International Normalized Ratio and said lower limit being about a 0.60 International Normalized Ratio, wherein said test strip is qualified if said results fall within said upper limit and said lower limit.

2. The system of claim 1, wherein said Program further comprises outputting a message to a user indicating test strip qualification.

3. A system for testing the qualification of a test strip for use to measure prothrombin (PT) time, said test strip comprising an assay reaction area and a control reaction area, said system comprising:
   a meter configured for receiving said test strip; and
   a computer-readable medium embodying a program to qualify said test strip according to a method comprising:
      obtaining PT results for said reaction areas; and
      comparing results from said control reaction area to control qualification criteria comprising an upper limit and a lower limit, each being dependent on assay reaction area PT results, wherein said test strip is qualified if said results fall within said upper limit and said lower limit.

4. The method of claim 3, wherein said upper and lower limits comprise line functions.

5. The method of claim 4, wherein said line functions are expressed as y=mx+b, wherein y represents an International Normalized Ratio results obtained for said control reaction area, x represents an International Normalized Ratio results obtained for said assay reaction area and m≈0.56 to 0.58 and b≈0.90 for said upper limit and wherein m ≈0.36 and b ≈0.37 to 0.38 for said lower limit.

6. The system of claim 5, wherein said program further comprises outputting a message to a user indicating test strip qualification.

7. A system for testing the qualification of a test strip for use to measure prothrombin (PT) time, said test strip comprising an assay reaction area, a first control reaction area and a second control reaction area, said system comprising:
   a meter configured for receiving said test strip; and
   a computer-readable medium embodying a program to qualify said test strip according to a method comprising:
      obtaining PT results for each said reaction areas; and
      comparing results from said first control reaction area to first control qualification criteria comprising a first upper limit and a first lower limit, said first upper limit being about a 1.9 International Normalized Ratio and said first lower limit being about a 0.60 International Normalized Ratio; and
      comparing results from said second control reaction area to second control qualification criteria comprising a second upper limit and a second lower limit, each being dependent on assay reaction area PT results;
      wherein said test strip is qualified if said results from said first control reaction area fall within said first upper limit and said first lower limit and if said results from said second control reaction area fall within said second upper limit and said second lower limit.

8. The system of claim 7, wherein said program further comprises outputting a message to a user indicating test strip qualification.

* * * * *